(12) United States Patent
Wei et al.

(10) Patent No.: US 6,887,400 B1
(45) Date of Patent: May 3, 2005

(54) WATER-SOLUBLE POLYAMINOAMIDES COMPRISING 1,3-DIIMINES AS SUNSCREEN AGENTS

(75) Inventors: Mingli Wei, Naperville, IL (US); Yin Z. Hessefort, Naperville, IL (US); Wayne M. Carlson, Batavia, IL (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 10/696,835

(22) Filed: Oct. 30, 2003

(51) Int. Cl.$^7$ ................................................ C09K 15/16
(52) U.S. Cl. ..................... 252/405; 252/588; 252/599; 524/86; 524/104; 524/105; 525/421; 525/422; 528/342; 528/335; 528/332; 528/336; 424/70.1; 424/70.2; 424/70.6; 424/70.7; 424/70.9; 424/70.11; 424/70.12; 424/70.22; 424/70.27
(58) Field of Search ................... 252/405, 588, 252/589; 424/70.1, 70.2, 70.6, 70.7, 70.9, 70.11, 70.12, 70.22, 70.27; 524/86, 104, 105; 528/342, 335, 332, 336; 525/421

(56) References Cited

U.S. PATENT DOCUMENTS

| | | |
|---|---|---|
| 2,914,427 A | 11/1959 | Valko et al. |
| 3,050,527 A | 8/1962 | Dearborn et al. |
| 3,183,207 A | 5/1965 | Nimoy et al. |
| 3,197,427 A | 7/1965 | Schmalz |
| 4,049,598 A | 9/1977 | Peerman et al. |
| 4,201,766 A | 5/1980 | Grollier et al. |
| 4,866,159 A | 9/1989 | Forestier et al. |
| 5,134,223 A | 7/1992 | Langer et al. |
| 5,350,796 A | 9/1994 | Devore et al. |
| 5,364,927 A | 11/1994 | Devore et al. |
| 6,222,006 B1 | 4/2001 | Kokko et al. |
| 6,352,613 B1 | 3/2002 | Maslanka |

FOREIGN PATENT DOCUMENTS

EP  0 320 121 A2  6/1989

OTHER PUBLICATIONS

Chen, L–W., Kuo, Y–H., "Synthesis and Properties of Polyamides Containing Imidazoline Rings", Macromol. Symp. 118, pp. 117–127, 1997.

Primary Examiner—David J. Buttner
Assistant Examiner—Christopher Keehan
(74) Attorney, Agent, or Firm—Michael B. Martin; Thomas M. Breininger

(57) ABSTRACT

A UV-protective composition comprising a water-soluble polyaminoamide containing 1,3-diimine groups, wherein the polyaminoamide containing 1,3-diimine groups absorbs ultraviolet light radiation having a wavelength of about 200 nm to about 420 nm, and methods of treating substrates with the UV-protective polyaminoamide containing 1,3-diimine groups.

20 Claims, No Drawings

WATER-SOLUBLE POLYAMINOAMIDES COMPRISING 1,3-DIIMINES AS SUNSCREEN AGENTS

TECHNICAL FIELD

This invention concerns compositions comprising polyaminoamides containing 1,3-diimine groups and methods of using the compositions to protect substrates from the harmful effects of ultraviolet radiation.

BACKGROUND OF THE INVENTION

Ultraviolet (UV) light radiation is known to be a factor that damages wood, paints and other protective or decorative coatings, plastics, various textiles made from natural and manmade fibers and keratin substrates including human skin and hair. Damage to human skin, for example, can include loss of skin elasticity and the appearance of wrinkles, erythema and skin burning and the inducement of phototoxic or photoallergic reactions. Hair damage by UV light is perceived as dryness, reduced strength, rough surface texture, loss of color and luster, stiffness and brittleness.

In the case of plastics, UV exposure can result in loss of tensile strength, embrittlement and discoloration. UV exposure can also result in fading of painted surfaces or dyed textiles. To help prevent such degradation, ultraviolet light stabilizers are often incorporated into a polymer composition, which is used as a protective top layer for underlying materials.

Protection of exposed skin and hair from UV exposure can be effected by applying directly to the skin and hair a preparation containing a UV-absorbing moiety.

Generally, sunscreens for application to the hair require substantivity(adhesion) to the hair, and compatibility in hair care formulations which are often water-based.

Many sunscreen agents, however, do not fully meet these requirements. Thus the level of sunscreen agents that could be incorporated into hair care formulations and/or the level of sunscreen agents that can deposit on the hair are limited. Accordingly, there is an ongoing need for new sunscreen agents with improved substantivity and water solubility for incorporation into aqueous formulations.

Skin and hair can also be protected by covering with clothing, thereby avoiding direct exposure of the skin and hair to sunlight. However, most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer. Therefore, there is also a need to provide protection against UV radiation for skin which lies underneath clothing, including lightweight summer clothing, which is undyed or dyed only in pale shades.

Commonly used UV absorbers such as benzotriazoles and benzophenone are highly effective in their UV absorber capacity. However, they are quite costly and can prove difficult to incorporate within different target media. Furthermore, UV absorbers of this type show no substantivity to hair and present handling difficulties in that they are generally produced and utilized in powder form and have relatively low melting points. A liquid, on the other hand, is much easier to handle, does not require melting, and provides more effective and thorough mixing throughout the target material.

Thus, there exists a continuing need for effective liquid UV absorbing compositions which exhibit sufficient versatility to be incorporated within or applied to different and various media and substrates.

SUMMARY OF THE INVENTION

This invention is a composition for protecting a substrate from the effect of ultraviolet light comprising an effective UV-protective amount of one or more water-soluble polyaminoamides containing 1,3-diimine groups, wherein the polyaminoamides containing 1,3-diimine groups absorb ultraviolet light radiation having a wavelength of about 200 nm to about 420 nm.

This invention is also a method of protecting a substrate from the effect of ultraviolet light comprising applying to the substrate an effective UV protective amount of a composition comprising an effective UV-protective amount of one or more water-soluble polyaminoamides containing 1,3-diimine groups, wherein the polyaminoamides containing 1,3-diimine groups absorb ultraviolet light radiation having a wavelength of about 200 nm to about 420 nm.

DETAILED DESCRIPTION OF THE INVENTION

This invention is a composition for protecting a substrate from the effect of ultraviolet light comprising an effective UV-protective amount of one or more novel water-soluble polyaminoamides containing 1,3-diimine groups.

"Polyaminoamide containing 1,3-diimine groups" means a polyaminoamide prepared as described herein that contains one or more groups of formula (I) which result from extended heating of a polyaminoamide at elevated temperatures relative to the temperature used in the formation of the polyaminoamide.

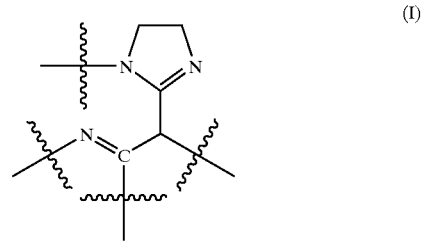

(I)

The synthesis of the polyaminoamide containing 1,3-diimine groups involves two stages of reactions. The first stage is the formation of polyaminoamide without targeted forming imidazoline and imine groups. The second stage is the formation of imidazoline ring and 1,3-diimine structures by prolonged heating at elevated temperatures (preferably >180° C.) that are much higher than the required temperatures for the first stage condensation reaction (normally below 160° C.). The heating at higher temperature promotes the formation of the imidazoline ring and imine group.

The 1,3-diimine group may be formed by an intramolecular or intermolecular reaction. The formation of a polyaminoamide containing a bicyclic 1,3-diimine resulting from an intramolecular reaction of a polyaminoamide comprising repeating diethylenetriamine (DETA) groups is shown in Scheme 1. The formation of a polyaminoamide containing 1,3-diimine units resulting from intermolecular reaction of polyaminoamides comprising repeating diethylenetriamine (DETA) groups is shown in Scheme 2.

Scheme 1

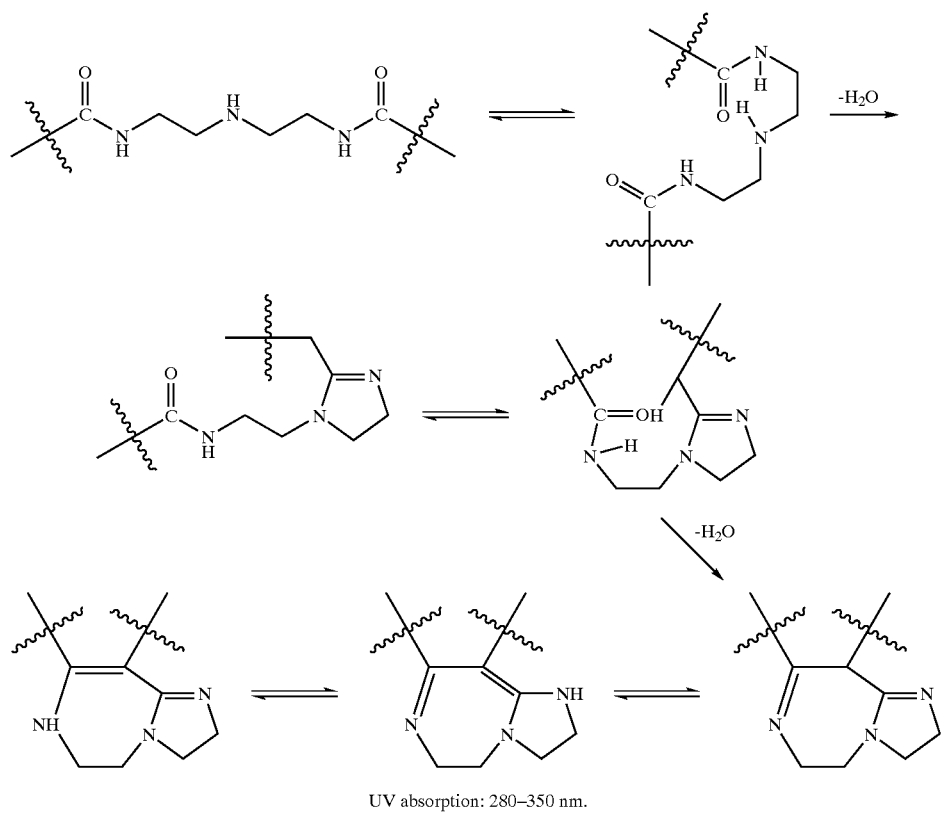

UV absorption: 280–350 nm.

Scheme 2

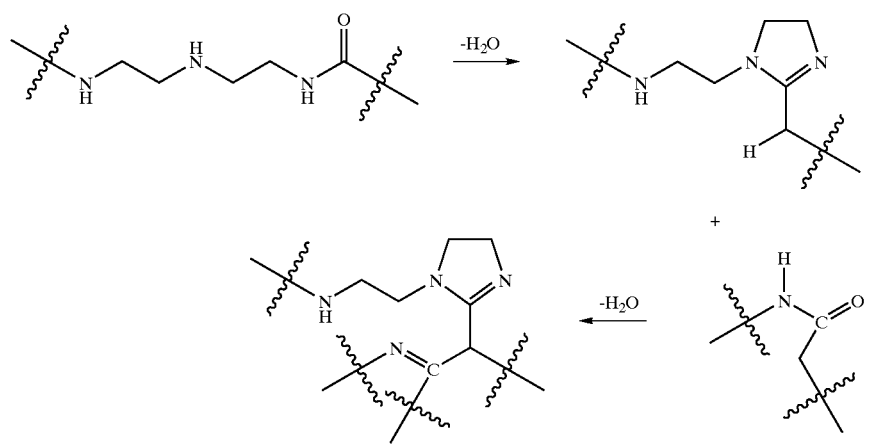

UV absorption: 28––350 nm.

The formation of bicyclic and exocyclic 1,3-diimine structures has been confirmed by NMR studies. The difference between the regular polyaminoamide polymers and 1,3-diimine containing polymers can be easily distinguished by three new peaks in its $^{13}C$ NMR. Regular polyaminoamide does not show UV absorption at 280–350 nm due to the lack of 1,3-diimine structure, the existence of 1,3-diimine can also be identified by the strong UV absorption around 300–350 nm due to its enamine-imine tautomerism equilibrium.

The water-soluble polyaminoamides used as a starting material for the polyaminoamides containing 1,3-diimide groups are well known in the art and can be prepared by the polycondensation of one or more organic dicarboxylic acid derivatives and one or more diamines. Representative polyaminoamides suitable for conversion into polyaminoamides containing 1,3-diimine groups include those described in U.S. Pat. Nos. 4,201,776, 4,866,159, 5,350,796, 6,222,006, 6,352,613, EP 0320121 and commonly assigned U.S. Ser. No. 10/655,163, filed Sep. 4, 2003.

The organic dicarboxylic acid derivative includes aliphatic or aromatic dicarboxylic acids and the corresponding diacid chlorides, anhydrides and esters thereof. Representative organic dicarboxylic acid derivatives include maleic acid, succinic acid, glutaric acid, adipic acid, pimelic acid, suberic acid, azelaic acid, sebasic acid, phthalic acid, isophthalic acid, terephthalic acid, naphthalenedicarboxylic acid, dimethyl maleate, dimethyl malonate, dimethyl succinate, diethyl glutarate, dimethyl adipate, dimethyl sebacate, dimethyl phthalate, dimethyl isophthalate, dimethyl terephthalate, dimethyl naphthalenedicarboxylate, dibasic esters (DBE), poly(ethylene glycol) bis(carboxymethyl) ether, succinyl chloride, glutaryl dichloride, adipoyl chloride, sebacoyl chloride, sebacate, phthaloyl chloride, isophthaloyl chloride, terephthaloyl chloride, naphthalenedicarboxylate, maleic anhydride, succinic anhydride, glutaric anhydride, phthalic anhydride, 1,8-naphthaic anhydride, and the like. Dimethyl terephthalate, adipic acid, DBE-2 dibasic ester are preferred.

The Diamine is selected from aliphatic or aromatic organic compounds having at least two amino (—NH$_2$) groups. Representative diamines include ethylene diamine, 1,2-diaminopropane, 1,3-diaminopropane, 1,4-diaminobutane, hexamethylenediamine (HMDA), 1,10-diaminodecane, phenylene diamine (all isomers), naphthalenediamine (all isomers), JEFFAMINE™ diamines, bis(aminoethyl)-N,N'-piperazine, bis(aminopropyl)-N,N'-piperazine, polyalkylene amines such as diethylenetriamine (DETA), triethylenetetraamine (TETA), tetraethylenepentaamine (TEPA), and the like. Diethylenetriamine is preferred.

In an aspect of this invention, terminal amino (—NH$_2$) groups in the polyaminoamide starting material or polyaminoamide containing 1,3-diimine groups may be end-capped with molecules containing UV absorbing moieties.

Representative molecules containing UV absorbing moieties include aromatic acyl or sulfonyl derivaties such as cinnamoyl, optionally substituted with one or more alkoxy group(s), p-dialkylaminobenzoyl, salicyloyl, acyl residues originating from a carboxylic or sulphonic acid derived from benzylidenecamphor, sulphonyl residues originating from isophthalylidenecamphor, acyl residues originating from a carboxylic or sulphonic acid derived from 2-arylbenzimidazoles, 2-arylbenzoxazoles, 2-arylbenzotriazoles, 2-arylbenzofurans, 2-arylindoles, acyl residues derived from an absorber of coumarinic carboxylic structure, sulphonyl residues originating from terephthalylidenecamphor, sulphonyl residues derived from benzylidenecamphor, substituted on the aromatic ring with one or more lower alkoxy radicals, acyl residues originating from a carboxylic or sulphonic acid derived from 2-arylbenzotriazoles, acyl residues derived from an absorber of mono- or diphenylcyanoacrylic structure, acyl residues derived from an absorber of an optionally substituted dibenzoylmethane structure, and the like.

Preferred molecules containing UV absorbing moieties include substituted and unsubstituted cinnamoyl, salicyloyl, and p-dialkylaminobenzoyl.

In a preferred aspect of this invention, the UV absorbing moiety absorbs UV radiation having a wavelength of about 280 nm to about 400 nm.

If desired, The polyaminoamide starting material or polyaminoamide containing 1,3-diimine groups may be crosslinked using one or more crosslinking agents. Preferred crosslinking agents include diepoxides, dianhydrides, dihalogen derivatives, diesters, diacids, epihalohydrins and epihalohydrin/amine oligomers. More preferred crosslinking agents include poly(ethylene glycol) diglycidyl ether, poly(propylene glycol) diglycidyl ether, epichlorohydrin and epichlorohydrin/dimethylamine oligomers.

The polyaminoamide containing 1,3-diimine groups may also be reacted with one or more modifiers selected from the group consisting of moieties containing cationic functional groups, moieties containing anionic functional groups and moieties containing substituted or unsubstituted aliphatic hydrocarbons in order to impart anionic, cationic or ampoteric properties to the polymer.

"Moieties containing cationic functional groups" include any molecule that contains a cationic functional group and also a group that is sufficiently reactive to form a covalent bond with one or more of the secondary amino groups of the polyaminoamide. Preferred moieties containing cationic functional groups include glycidyltrimethylammonium chloride, N-(3-chloro-2-hydroxypropyl) trimethylammonium chloride, and the like.

"Moieties containing anionic functional groups" include any molecule that contains an anionic functional group and also a group that is sufficiently reactive to form a covalent bond with one or more of the secondary amino groups of the polyaminoamide. Preferred moieties containing anionic functional groups include chloroacetic acid and salts thereof, 1,3-propane sultone, 1,4-butane sultone, and the like.

Moieties containing substituted or unsubstituted aliphatic hydrocarbons typically have formula R—X, wherein X is halogen, epoxide, acyl, anhydride, acid, ester, halohydrin and R is any linear or branched, saturated or unsaturated, substituted or non-substituted aliphatic hydrocarbon. Preferred moieties containing substituted or unsubstituted aliphatic hydrocarbons include glycidyl ethers of $C_6$–$C_{18}$ aliphatic alcohols.

In another aspect, this invention is a composition for protecting a substrate from the effect of ultraviolet light comprising an effective UV-protective amount of one or more water-soluble polyaminoamides containing 1,3-diimine groups, wherein said polyaminoamides containing 1,3-diimine groups absorb ultraviolet light radiation having a wavelength of about 200 nm to about 420 nm.

In a preferred aspect of this invention, the polyaminoamide is blended with one or more cosmetically acceptable excipients to prepare a composition for applying to keratin substrates including hair, skin and nails.

Typical compositions for applying to keratin substrates comprise about 0.1 to about 10 weight percent of water-soluble polyaminoamide, based on the weight of the composition.

In a preferred aspect of this invention, the keratin substrate is skin.

In another preferred aspect, the keratin substrate is hair.

An advantage of the polyaminoamide of this invention is that the polymer can alternately contain cationic, anionic and/or ampholytic (or amphoteric) characteristics resulting in a a 'multi-functional' nature that offers hair and skin conditioning advantages and improves the polymer's performance in conditioning, dye retention, etc.

"Cosmetically acceptable excipient" means a non-toxic, non-irritating substance which when mixed with the UV-absorbing polymer of this invention makes the polymer more suitable to be applied to skin or hair.

In another preferred aspect, the excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids. Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquatemium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578–611 (1994) which is incorporated entirely by reference. Complex carbohydrates found in Kirk-Othmer *Encyclopedia of Chemical Technology*, Fourth Edition, Vol. 4, John Wiley and Sons, NY pp. 930–948, 1995 which is herein incorporated by reference.

Typical compositions for applying to keratin substrates comprise about 1 to about 3 weight percent, based on polymer actives, of the polyaminoamide containing 1,3-diimine groups of this invention.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used in this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, cocotrimonium chloride, cethethyldimonium bromide, dibehenyldimonium chloride, dihydrogenated tallow benzylmonium chloride, disoyadimonium chloride, ditallowdimonium chloride, hydroxycetyl hydroxyethyl dimonium chloride, hydroxyethyl behenamidopropyl dimonium chloride, hydroxyethyl cetyldimonium chloride, hydroxyethyl tallowdimonium chloride, myristalkonium chloride, PEG-2 oleamonium chloride, PEG-5 steammonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquatemium-6, Polyquatemium-7, Polyquatemium-10, Polyquatemium-22, Polyquatemium-37, Polyquatemium-39, Polyquatemium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41–42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include ceteareth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning®, Midland, Mich., USA. Additional alkyl and phenyl silicones may be employed to enhance moisturizing properties. Resins such as dimethicone (and) trimethylsoiloxysilicate, known as Dow Corning® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquatemium-10, Guar hydroxypropyltrimonium chloride, Starch hydroxypropyltrimonium chloride, Polyquatemium-4, Polyquatemium-5, Polyquaternium-6, Polyquaternium-7, Polyquatemium-14, Polyquatemium-15, Polyquaternium-22, Polyquaternium-24, Polyquaternium-28, Polyquaternium-32, Polyquaternium-33, Polyquaternium-36, Polyquatemium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10–30 Alkyl Acrylate Crosspolymer, such as the Carbopol® and Pemulen® series, both available from B.F. Goodrich, Akron, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28, available from International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate.

The antioxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3, 3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, Ondeo Nalco Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

In a preferred aspect, the cosmetically acceptable composition of this invention is selected from products for treating hair, including shampoos, sunscreens, conditioners, permanent waves, hair relaxers, hair bleaches, hair detangling lotion, styling gel, styling glazes, spray foams, styling creams, styling waxes, styling lotions, mousses, spray gels, pomades, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

In another preferred aspect, the cosmetically acceptable composition is selected from compositions for treating skin including leave-on or rinse-off skin care products such as lotions, hand and body creams, liquid soaps, bar soaps, bath oil bars, facial cleanser, aftershaves, shaving gels or shaving creams, mascara, eye gel, eye lotion, body washes, deodorants, anti-perspirants, sunscreens, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/tacrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyratelbutyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

If the compositions of the instant invention are intended for use in the dyeing of keratin fibers, and in particular human hair, they generally contain at least one oxidation dyestuff precursor and/or one direct dyestuff, in addition to the unsaturated quaternary ammonium compounds. They also can contain any other adjuvant normally used in this type of composition.

The pH of the dyeing compositions is generally 7 to 11 and can be adjusted to the desired value by adding an alkalizing agent.

The compositions according to this invention also can be used for waving or straightening the hair. In this case, the composition generally contains, in addition to these unsaturated quaternary ammonium compounds, one or more reducing agents and, if appropriate, other adjuvants normally used in this type of composition; such compositions are intended for use conjointly with a neutralizing composition.

As discussed above, the novel polyaminoamides containing 1,3-diimine groups of this invention are also useful as ultraviolet light absorber agents for stabilizing a wide variety of materials including, for example, various polymers (both crosslinked and thermoplastic), photographic materials and dye solutions for textile materials, as well as in ultraviolet light screening agents. The polyaminoamides containing 1,3-diimine groups can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition.

The polyaminoamides containing 1,3-diimine groups of this invention can be employed to stabilize polymeric materials as well as a variety of naturally occurring and synthetic organic materials which are subject to degradation by ultraviolet radiation by incorporation of the polyaminoamides containing 1,3-diimine groups into the polymeric materials, either chemically or physically.

Representative polymers which may be stabilized include, but are not limited to polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; and epoxymelamine resins.

The novel polyaminoamides containing 1,3-diimine groups of this invention may be used in widely varying amounts in such applications depending upon such things as the material to be stabilized and the particular application. However, when employed as a stabilizing additive for materials such as organic polymers, the polyaminoamide UV absorbers of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the polyaminoamide UV absorbers are utilized in the same relative amounts but based on the total weight of the screening agent.

The polyaminoamides containing 1,3-diimine groups can also be added to the polymers to be stabilized in the form of a masterbatch which comprises these compounds, for example, in a concentration of from about 2.5 to about 25%, preferably from about 5 to about 20% by weight of the polymer.

The polyaminoamides containing 1,3-diimine groups can be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent.

The polymers incorporating the polyaminoamide containing 1,3-diimine groups of this invention can be incorporated into articles of manufacture by any method conventional in the art including molding, extrusion, and the like.

The polyaminoamides containing 1,3-diimine groups of this invention are also suitable for the photochemical stabilization of undyed, dyed or printed fiber materials including, silk, leather, wool, polypropylene, polyester, polyethylene, polyolefins, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. The polyamides are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which such textile materials offer to the human skin. An additional preferred area includes automotive applications such as seat belts, headliners, carpeting, and upholstery.

The polyaminoamide containing 1,3-diimine groups is applied to the textile fiber material by any of the customary dyeing methods, typically in an amount of 0.01 to 5 percent by weight, based on the weight of the fiber material.

The polyaminoamide containing 1,3-diimine groups can be applied to the fiber material in various ways and fixed on the fiber, especially in the form of aqueous dispersions or printing pastes.

The textile fiber materials finished with the polyaminoamide containing 1,3-diimine groups of this invention possess improved protection against photochemical breakdown of the fiber and yellowing phenomena and, in the case of dyed fibre material, are of enhanced light fastness. Particular emphasis should be drawn to the greatly improved photoprotective effect of the treated textile fiber material and, in particular, the good protective effect with respect to short-wave UV-B rays. This is manifested by the fact that the textile fiber material finished with the polyaminoamide containing 1,3-diimine groups has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with the polyaminoamide containing 1,3-diimine groups are permeable to UV radiation. The determination of the sun protection factor of textile fiber materials is explained, for example, in WO94/04515 or in J. Soc. Cosmet. Chem. 40, 127–133 (1989) and can be carried out analogously thereto.

The polyaminoamide containing 1,3-diimine groups of this invention can be used in coating compositions and can be applied to any desired substrate, for example to metal, wood, plastic, fiberglass or ceramic materials. The coating compositions can be pigmented mono-coats or multi-layer (primer/basecoat/clearcoat) systems typical of automotive finishes.

The coating compositions can be applied to the substrates by the customary methods, for example by brushing, spraying, pouring, dipping or electrophoresis; see also Ullmann's Encyclopedia of Industrial Chemistry, 5th Edition, Vol. A118, pp. 491–500.

The polyaminoamide containing 1,3-diimine groups may also be applied topically by polishing a surface with a composition comprising the polyaminoamide containing 1,3-diimine groups and an inert carrier such as solvent, silicone oil in water emulsions, or automotive paint wax, e.g. Carnauba wax. These topical treatment compositions may be used to stabilize coating films, fabrics, leather, vinyl and other plastics and wood.

Mixtures comprising polyaminoamides containing 1,3-diimine groups of this invention can also be used as stabilizers for film-forming binders for coatings, for example for paints as disclosed in, for example, U.S. Pat. Nos. 4,619,956, 4,740,542, 4,826,978, 4,962,142, 5,106,891, 5,198,498, 5,298,067, 5,322,868, 5,354,794, 5,369,140, 5,420,204, 5,461,151 and 5,476,937, EP-0434608 and EP-A-0444323), particularly coatings and paints for the automobile industry.

Such film forming compositions typically comprise about 0.01 to about 20 percent by weight of the polyaminoamide containing 1,3-diimine groups of this invention.

The polyaminoamides containing 1,3-diimine groups of this invention can also be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

The polyaminoamides containing 1,3-diimine groups can be combined with other UV absorbers, especially those which are dispersible in aqueous gelatin, for example with hydroxyphenylbenzotriazoles (cf. for example U.S. Pat. Nos. 4,853,471, 4,973,702, 4,921,966 and 4,973,701), benzophenones, bisbenzophenones as described in U.S. Pat. No. 6,537,670, oxanilides, cyanoacrylates, salicylates, or acrylonitriles or thiazolines. In this context it is advantageous to employ these further UV absorbers in the photographic material in layers other than those comprising the polyaminoamides containing 1,3-diimine groups.

The polyaminoamides containing 1,3-diimine groups of this invention can also be used in cellulose-based paper formulations, e.g., in newsprint, cardboard, posters, packaging, labels, stationery, book and magazine paper, bond typing paper, multi-purpose and office paper, computer paper, xerographic paper, laser and inkjet printer paper, offset paper, currency paper, etc.

The polyaminoamides containing 1,3-diimine groups of this invention are also suitable for the stabilization of ink.

Depending upon their ultimate end use, the polyaminoamides containing 1,3-diimine groups of this invention may be combined with one or more of a variety of additives conventionally employed in the UV stabilizing art including antioxidants, ultraviolet light absorbers, ultraviolet light stabilizers, metal deactivators, phosphites, phosphonites, hydroxylamines, nitrones, thiosynergists, peroxide scavengers, polyamide stabilizers, nucleating agents, fillers, reinforcing agents, plasticizers, lubricants, emulsifiers, pigments, rheological additives, flameproofing agents, antistatic agents, blowing agents, benzofuranones and indolinones.

The foregoing may be better understood by reference to the following Examples, which are presented for purposes of illustration and are not intended to limit the scope of this invention.

EXAMPLE 1

Diethylenetriamine-DBE-2 Dibasic Ester Polyaminoamide Containing 1,3-diimine Groups.

In a 5-neck 1000 ml two-piece resin reactor equipped with a mechanical stirrer, nitrogen purge, temperature controller and condenser is charged 208.0 g diethylenetriamine (DETA, 2.0 moles), 327 g (2.0 moles) DBE-2 dibasic ester and 5.0 g sulfuric acid. The mixture is heated to 150° C. and methanol is collected through a condenser. The temperature is raised to 180° C. once no additional methanol is distilled out. The temperature is maintained at at least 180° C. for several hours until about 15.0 g of byproduct water is collected. Heating is then stopped and 395 g water is slowly added into the reactor at a temperature below about 140° C. to make an aqueous polymer solution.

EXAMPLE 2

Diethylenetriamine-Dimethyl Terephthalate-DBE-2 Dibasic Ester Polyaminoamide Containing 1,3-diimine groups.

To a reactor as described in Example 1 is charged 87.3 g (0.45 mole) dimethyl terephthalate and the reactor is purged with nitrogen for 15 minutes. DETA (156.4 g, 1.5 moles), DBE-2 dibasic ester and 5.0 g sulfuric acid are charged into the reactor. The mixture is heated at 150° C. for about 2 hours until no methanol is distilled off. The temperature is then raised to 190° C. The temperature is kept at 190° C. or higher for several hours until about 15.0 g of byproduct water is collected. Heating is then stopped and 300 g water is slowly added into the reactor at a temperature below about 140° C. to make an aqueous polymer solution.

EXAMPLE 3

Diethylenetriamine-Dimethyl Terephthalate-DBE-2 Dibasic Ester-Methyl Salicylate Polyaminoamide Containing 1,3-diimine Groups.

To a reactor as described in Example 1 is charged 58.3 g (0.3 mole) dimethyl terephthalate and the reactor is purged with nitrogen for 15 minutes. DETA (171.6 g, 1.65 moles), 196.2 g (1.2 moles) DBE-2 dibasic ester, and 5.0 g sulfuric acid are charged into the reactor. The mixture is heated at 150° C. until no methanol is distilled off. Methyl salicylate 45.3 g (0.3 mole) is added into the reactor. The mixture is further heated at 150° C. until no methanol is distilled off. The temperature is then raised to 190° C. and maintained at 190° C. or higher until about 15 g of byproduct water is collected. Heating is then stopped and 300 g water is slowly added into the reactor at a temperature below about 140° C. to make an aqueous polymer solution.

EXAMPLE 4

Diethylenetriamine-Adipic Acid Polyaminoamide Containing 1,3-diimine Groups.

To a reactor as described in Example 1 is charged 208.0 g (2.0 moles) of DETA and 292 g (2.0 moles) of adipic acid. The mixture is heated to 160° C. and water is collected through a condenser. The temperature is raised to 185° C. after about 72.0 g water (4.0 moles) is collected. The temperature is maintained at at least 185° C. until about 15.0 g of byproduct water is collected.

Heating is then stopped and 410 g water is slowly added into the reactor at a temperature below about 140° C. to make an aqueous polymer solution.

EXAMPLE 5

Tetraethylenepentamine-Adipic Acid Polyaminoamide Containing 1,3-diimine Groups.

To a reactor as described in Example 1 is charged 330.0 g (1.65 moles) of tetraethylenepentamine (TEPA) and 219.0 g (1.50 moles) of adipic acid. The mixture is heated to 190° C. and byproduct water is collected through a condenser. The temperature is maintained at at least 190° C. for several hours until 72.0 g (4.0 moles) or more of byproduct water is collected.

Heating is then stopped and 410 g water is slowly added into the reactor at a temperature below about 140° C. to make an aqueous polymer solution.

EXAMPLE 6

Comparative Example

In this example, DETA is condensed with DBE-2 dibasic ester or adipic acid using procedures similar to those described in Examples 1–5, except for heating for the times and temperatures indicated in Table 1. The UV absorbance (measured at 100 ppm polymer solution in 1 cm cell, and $\lambda$max=313 nm) of the polymer is recorded after heating for 2 hours at 150° C. The polymer is then heated for an additional period at the temperatures shown in column 4 and the UV absorbance of the polymer is again recorded.

TABLE 1

UV Absorbance and Synthetic Conditions of Polyaminoamides containing 1,3-Diimine Groups

| Example | Starting Materials | Absorbance of Prepolymer | Absorbance of New Polymer |
|---|---|---|---|
| Example A | DETA/DBE-2 | <0.01 (2 hrs at 150° C.) | 0.507 (4.5 hrs at 180° C.) |
| Example B | DETA/DBE-2 | <0.01 (2 hrs at 150° C.) | 0.767 (2.0 hrs at 220° C.) |
| Example C | DETA/Adipic Acid | <0.05 (2.0 hrs at 150° C.) | 0.270 (6.0 hrs at 165° C.) |
| Example D | DETA/Adipic Acid | <0.05 (2.0 hrs at 150° C.) | 1.374 (5.0 hrs at 185° C.) |

Table 1 shows the emergence of UV absorbance after the preformed polymers at lower temperatures were heated at higher temperatures. Conventional polyaminoamides do not show meaningful UV absorbance at 280–350 nm due to the lack of 1,3-diimine structure, the existence of 1,3-diimine is easily identified by the strong UV absorbance around 300 nm–350 nm due to the enamine-imine tautomerism equilibrium.

EXAMPLE 7
Representative Surfactant Treatment Formulation.

A representative surfactant testing solution is shown in Table 2. The formulation is prepared by mixing water and sodium lauryl sulfate. Polymer is then added into the surfactant solution. The pH of surfactant solution is adjusted to 5.0+/−0.2 with citric acid.

TABLE 2

Representative Surfactant Testing Solution

| Ingredients (INCI Name) | % w/w |
|---|---|
| Water | Qs to 100 |
| Sodium Lauryl Sulfate | 10 (solid) |
| Polymeric Sunscreens | 2.0 (solid) |

EXAMPLE 8
Representative Hair Conditioner Formulation.

A representative leave on hair conditioner formulation is shown in Table 3. The conditioner is prepared by dispersing the Natrosol in water, adding polymer and mixing until uniform. Panthanol and cetrimonium chloride are then added with mixing after each addition. The parabens are combined with glycerin and the mixture is stirred until uniform and then added to the batch. Polysorbate 20 and any fragrance are combined, mixed until uniform and the mixture is added to the batch. Finally, the pH of the batch is adjusted to about 5.3

TABLE 3

Representative Leave-On Conditioner Formulation

| Ingredients (INCI Name) | % w/w |
|---|---|
| Water | Qs to 100 |
| Hydroxyethylcellulose | 0.8 |
| Polymeric Sunscreens | 0.7 |
| Panthanol | 0.7 |
| Cetrimonium Chloride | 2.0 |
| Glycerin | 1.0 |
| Methyl Paraben | 0.2 |

TABLE 3-continued

Representative Leave-On Conditioner Formulation

| Ingredients (INCI Name) | % w/w |
|---|---|
| Propyl Paraben | 0.02 |
| Polysorbate 20 | 0.5 |

EXAMPLE 9
Representative Shampoo Formulation.

The ingredients shown in Table 4 are added to water in the sequence shown with mixing at a moderate mixing speed. The polymeric sunscreen is then added, the pH is adjusted to about 0.6 with citric acid (0.25–0.4 wt %) and sodium chloride is added with mixing to obtain the desired viscosity.

TABLE 4

Representative Shampoo

| Ingredient | INCI Designation | % w/w |
|---|---|---|
| Water | Water | qs |
| Standapol EA-1 | Ammonium Laureth Sulfate | 43 |
| Mirataine CB | Cocamidopropyl Betaine | 9.3 |
| Hamposyl L-30 | Sodium Lauroyl Sarcosinate | 5.0 |
| Polymeric Sunscreen | Polymeric Sunscreen | 4 |
| Preservative | Preservative | qs |
| Citric Acid | Citric Acid | Qs to pH = 6 |
| Sodium Chloride | Sodium Chloride | 1.0 |
| Fragrance | Fragrance | 0.05 |

EXAMPLE 10
Preparation of Hair Tresses for Testing.

The experiments described herein are performed on eight-inch long Virgin/Blond hair tresses, available from International Hair Importers and Products Inc., Bellerose, N.Y.

The hair tresses (1.5 g each) are bundled and wetted with water. One gram of sodium laureth sulfate is massaged onto the hair tresses from top to bottom for 1 minute. The hair tresses are then rinsed under 40° C. tap water for 1 minute, soaked in deionized water overnight and air-dried.

EXAMPLE 11
Preparation of Colored Hair Tresses for Testing.

Eight-inch long medium brown and bleached hair tresses from International Hair Importers and Products Inc., Bellerose, N.Y., are used. Hair is dyed to auburn red using a level 3 commercial dyeing kit from L'Oreal. The dye procedures follow the instructions from the dye kit.

EXAMPLE 12
UV Irradiation.

Before UV exposure, the hair tresses are treated with formulations from the examples shown above for 5 minutes, then rinsed under deionized water for 30 seconds. The treated hair is air dried. The treatment is repeated 3 times.

After treatment, the hair tresses are untied from bundle and spread on sample holders in a single layer. The samples are placed 10 cm away from UV bulbs and exposed to simulated summer-noon sunlight in the Q-Panel Accelerated Weathering Tester (Q-Panel Lab Products, 26200 First Street Cleveland, Ohio 44145) at 45° C. and 30% relative humidity for 400 to 600 hours.

EXAMPLE 13

Colorimeter Measurement.

The hair samples collected from the UV weathering tester are bundled. The colorimeter (LabScan XE, HunterLab, Reston, Va.) is standardized before the test. A hair bundle is placed on the top of scanning port and the hair samples are read. Hunter tristimulus L, a, b values are measured by the use of a Hunter Colorimeter LabScan XE instrument. The reported data, in terms of total color difference, $\Delta E=\sqrt{(9\Delta l^2 + \Delta a^2 + \Delta b^2)}$ and chromaticity difference $\Delta C=4\ (Aa^{2+}\ Ab^2)$ between unexposed and exposed sections of a hair tress under UV irradiation are the average of measurements performed at several positions. The index of coloration is calculated as $CI=\Delta E/\Delta C$

EXAMPLE 14

Tensile Strength Test.

The hair tensile strength is the direct reflection the degree of photo damage to the hair. The strength of hair can be measured using a suitable tensile testing instrument. Individual hairs are mounted in a jig and pulled at a fixed rate until breakage occurs. The load is applied under computer control and the load against extension is recorded for each hair. Using measured hair diameters and a fixed gauge length, this data can be converted to total amount of work needed to break the hair fiber. The instrument used to measure the hair tensile strength is DiaStron Miniature Tensile Testers 170/670 (DiaStron limited, Hamphsire, UK).

EXAMPLE 15

FT-IR Analysis.

FTIR has been used to determine the degree of UV damage to hair. UV damage can be observed via the SO band as a result of oxidation of S—S link in cysteine or cystine. By taking the band ratio of SO (1041 $cm^{-1}$) and amide band located at (1633 $cm^{-1}$) at different time points, the increase of the SO band intensity can be measured quantitatively. The intensity of the SO band is directly proportional to the length of UV exposure at the first 800 hours. It reaches plateau between 800 to 1200 hours exposure. The study has shown the FTIR method is a viable technique to quantitatively measure the relative change of the SO band.

The FT-IR study is performed by pressing a tress of virgin hair on a single reflectance cell with a presser along the same axis as the beam path. The hair is scanned 128 times using a Nicolet Avatar 360 FTIR. The detector employed is DTGS. The spectrum collected is designated as 0 hour exposure. Subsequent FTIR analyses are performed on the hair in the same fashion after UV exposure of 400, 800 and 1200 hours. Peak height of the SO band at 1041 $cm^{-1}$ is measured and compared with the amide I band (1633 $cm^{-1}$). A higher peak ratio means more oxidation of the UV damaged hair. Each tress is analyzed in triplicate to obtain an average value.

EXAMPLE 16

Demonstration of Hair Coloration Deduction.

In order to demonstrate the effectiveness of the UV-absorbing polymers in reducing hair coloration after UV exposure, quantitative changes in total color difference between exposed and unexposed hair tresses and between tresses treated with a representative UV-absorbing polymer of this invention and tresses treated with a comparative product prepared using polyquaterniurn 59 and butylene (Comparative Sunscreen A) are measured. The results are shown in Tables 5 and 6 for tresses treated with the formulations of Examples 7 and 8, respectively.

TABLE 5

Measurement of Coloration Index

| Sample Name | L | a | b | Delta E |
|---|---|---|---|---|
| Virgin | 40.4 | 6.1 | 16.5 | |
| Control | 45.01 | 6.78 | 21.16 | 15.47 |
| Polymeric Sunscreen | 44.15 | 7.01 | 20.89 | 12.94 |
| Comparative Sunscreen A | 45.21 | 6.86 | 20.62 | 15.90 |

As shown in Table 5, polymeric sunscreens prepared using UV-absorbing polymers of this invention show a much lower total color difference (AE) than the untreated hair sample. The result indicates that the polymeric sunscreens of this invention provide superior protection of hair from changing color after UV exposure.

TABLE 6

Measurement of Coloration Index

Leave On Conditioner

| Sample Name | L | a | b | Delta E |
|---|---|---|---|---|
| Virgin | 40.4 | 6.1 | 16.5 | |
| Control | 46.56 | 6.78 | 21.14 | 19.05 |
| 5299-78 | 44.91 | 6.86 | 20.68 | 14.18 |
| Comparative Sunscreen A | 46.04 | 6.92 | 21.11 | 17.55 |

As shown in Table 6, a conditioner formulated with a representative polymeric sunscreen of this invention provides better sun protection than comparative sunscreen A, as evidenced by the lower total color change in conditioner treated hair tresses

EXAMPLE 17

Demonstration of Hair Coloration Deduction for Dyed Hair.

Quantitative changes are measured in total color difference of the dyed hair tresses between exposed and unexposed hair tresses and between tresses treated with a representative UV-absorbing polymer of this invention and with comparative products, particularly polyquaternium 59 and butylene (Comparative Sunscreen A), commercial product Biolage® and Clariol Hydrience®. The results are shown in Table 7.

TABLE 7

Measurement of Total Color Change for Dyed Hair

| After UV Exposure | L | a | b | Delta E | Delta C |
|---|---|---|---|---|---|
| Control, 987-1 | 31.18 | 11.11 | 18.02 | 25.20 | 7.20 |
| Polymeric Sunscreen | 30.25 | 12.03 | 17.25 | 17.72 | 5.07 |
| Biolage ®, Commercial | 31.16 | 10.95 | 18.70 | 22.49 | 7.25 |
| Clariol Hydrience ® | 30.84 | 11.72 | 17.94 | 23.53 | 7.83 |
| Comparative Sunscreen A | 32.91 | 10.905 | 18.73 | 24.30 | 7.40 |

In table 7, commercial products for hair color fading protection are used as benchmarks. The results reported at Table 7 clearly indicate that the manually dyed hair tresses treated with polymeric sunscreen show much lower delta E value than comparative sunscreen A and commercial products, which means that polymeric sunscreen provides better color fading protection for artificial hair dye.

EXAMPLE 18

Tensile Strength Results.

The breakage resistance of single fibers directly reflects the degree of the hair damage caused by sun light. The higher force required to break a single fiber, the less damage the hair fiber undergoes. The following table summarizes the test results of the single fiber analysis which uses 70 pieces of hair fibers for each study to generate statistically sound data.

TABLE 8

Tensile Strength Analysis

| Sample Name | Total work (mJ) | % Enhancement |
|---|---|---|
| Undamaged | 6.69 | |
| Damaged | 4.12 | |
| Polymer 1 | 4.9 | 30.3 |
| Polymer 2 | 4.89 | 30.3 |
| Comparative Sunscreen A | 4.46 | 13.2 |

As shown in Table 8, polymeric sunscreens 1 and 2 show significantly higher breaking force than comparative sunscreen A. The results also prove that polymeric sunscreens 1 and 2 provide better sun protection than control (damaged) and benchmark.

EXAMPLE 19

FT-IR Analysis.

The oxidation of the disulfide bond is an indication of the degree for the photodegradation of hair keratin. FT-IR analysis measures the absorbance of the S—O bond using amide from hair protein as an internal standard. The results (Tables 9 and 10) show that hair tresses protected by polymeric sunscreens of this invention have smaller SO/amide ratios than comparative Sunscreen A and control. Two different sets of hair tresses treated with conditioner formulation are tested to see the duplicity. The results shown in Tables 9 and 10 confirm that the polymeric sunscreen of this invention performs better than control and comparative sunscreen A.

TABLE 9

FT-IR Analysis

| Sample Name | Ratio of S—O/Amide | Average |
|---|---|---|
| Control | 0.574 | |
| | 0.621 | |
| | 0.59 | 0.601 |
| | 0.581 | |
| | 0.641 | |
| Polymeric Sunscreen | 0.516 | |
| | 0.509 | |
| | 0.482 | 0.502 |
| | 0.469 | |
| | 0.533 | |
| Comparative Sunscreen A | 0.705 | |
| | 0.654 | |
| | 0.722 | 0.673 |
| | 0.595 | |
| | 0.692 | |

TABLE 10

FT-IR Analysis

| Sample Name | Ratio of S-O/Amide | Average |
|---|---|---|
| Control | 0.605 | |
| | 0.638 | |
| | 0.66 | 0.656 |
| | 0.74 | |
| | 0.639 | |
| Polymeric Sunscreen A | 0.528 | |
| | 0.506 | |
| | 0.529 | 0.519 |
| | 0.511 | |
| | 0.519 | |
| Comparative Sunscreen A | 0.692 | |
| | 0.619 | |
| | 0.588 | 0.624 |
| | 0.606 | |
| | 0.617 | |

Changes can be made in the composition, operation and arrangement of the method of the invention described herein without departing from the concept and scope of the invention as defined in the claims.

What is claimed is:

1. A composition for protecting a substrate from the effect of ultraviolet light comprising an effective UV-protective amount of one or more water-soluble polyaminoamides containing 1,3-diimine groups, wherein the polyaminoamides containing 1,3-diimine groups absorb ultraviolet light radiation having a wavelength of about 200 nm to about 420 nm.

2. The composition of claim 1 wherein the polyaminoamides containing 1,3-diimine groups absorb UV radiation having a wavelength of about 280 nm to about 350 nm.

3. The composition of claim 1 wherein the polyaminoamide containing 1,3-diimine groups further comprises one or more additional uv absorbing moieties.

4. The composition of claim 3 wherein the additional uv absorbing moieties are selected from substituted and unsubstituted cinnamoyl, salicyloyl, and p-dialkylaminobenzoyl.

5. The composition of claim 1 wherein the polyaminoamide containing 1,3-diimine groups is cross linked with one or more crosslinking agents.

6. The cross-linked polyaminoamide containing 1,3-diimine groups according to claim 5, wherein the crosslinking agents are selected from the group consisting of diepoxides, dianhydrides, dihalogen derivatives, diesters, diacids, epihalohydrins and epihalohydrinlamine oligomers.

7. The cross-linked polyaminoamide containing 1,3-diimine groups according to claim 6 wherein the crosslinking agent is selected from the group consisting of poly (ethylene glycol) diglycidyl ether, poly(propylene glycol) diglycidyl ether, epichlorohydrin, epichlorohydrin/ dimethylamine oligomers.

8. A modified polyaminoamide containing 1,3-diimine groups prepared by reacting a polyaminoamide containing 1,3-diimine groups according to claim 1 with one or more modifiers selected from the group consisting of moieties containing cationic functional groups, moieties containing anionic functional groups and moieties containing substituted an unsubstituted aliphatic hydrocarbons.

9. The modified polyaminoamide containing 1,3-diimine groups according to claim 8 wherein the moiety containing cationic functional groups is selected from glycidyltrimethylammonium chloride and N-(3-chloro-2-hydroxypropyl) trimethylammonium chloride.

10. The modified polyaminoamide containing 1,3-diimine groups according to claim 8 wherein the moiety containing anionic functional groups is selected from chloroacetic acid and salts thereof, 1,3-propane sultone, 1,4-butane sultone.

11. The modified polyaminoamide containing 1,3-diimine groups according to claim 8 wherein the moiety containing aliphatic hydrocarbon groups is selected from the group consisting of glycidyl ethers of $C_6$–$C_{18}$ aliphatic alcohols.

12. The composition of claim 1 further comprising one or more cosmetically acceptable excipients.

13. The composition of claim 12 wherein the excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

14. The composition of claim 12 selected from the group consisting of shampoos, sunscreens, conditioners, permanent waves, hair relaxers, hair bleaches, hair detangling lotion, styling gel, styling glazes, spray foams, styling creams, styling waxes, styling lotions, mousses, spray gels, pomades, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

15. The composition of claim 12 selected from the group consisting of lotions, hand and body creams, liquid soaps, bar soaps, bath oil bars, facial cleanser, aftershaves, shaving gels, shaving creams, mascara, eye gel, eye lotion, body washes, deodorants, antiperspirants, sunscreens, suntan lotions, after sun gels, bubble baths and hand and mechanical dishwashing compositions.

16. A method of protecting a substrate from the effects of ultraviolet light comprising applying to the substrate an effective ultraviolet light protective amount of the polyaminoamide containing 1,3-diimine groups of claim 1.

17. The method of claim 16 wherein the substrate is a keratin substrate.

18. The method of claim 17 wherein the keratin substrate is skin.

19. The method of claim 17 wherein the keratin substrate is hair.

20. The method of claim 16 wherein the substrate is selected from the group consisting of textile fiber materials, metal, wood, ceramics, plastics and paint.

* * * * *